(12) United States Patent
Wick (10) Patent No.: US 8,309,029 B1
(45) Date of Patent: Nov. 13, 2012

(54) VIRUS AND PARTICULATE SEPARATION FROM SOLUTION

(75) Inventor: Charles H. Wick, Darlington, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 612 days.

(21) Appl. No.: 12/411,679

(22) Filed: Mar. 26, 2009

(51) Int. Cl.
*G01N 15/06* (2006.01)
*G01N 33/00* (2006.01)
*G01N 33/48* (2006.01)

(52) U.S. Cl. ............... 422/83; 422/50; 422/88; 422/93; 422/98; 436/43

(58) Field of Classification Search ............... 422/50, 422/83, 88, 93, 98; 436/43
See application file for complete search history.

(56) References Cited

U.S. PATENT DOCUMENTS

| 4,972,957 | A | * | 11/1990 | Liu et al. ....................... 209/143 |
| 5,117,190 | A | * | 5/1992 | Pourprix ....................... 324/452 |
| 5,207,877 | A | * | 5/1993 | Weinberg et al. ............. 423/210 |
| 5,542,967 | A | * | 8/1996 | Ponizovsky et al. ............. 96/82 |
| 5,855,652 | A | * | 1/1999 | Talley ............................... 96/44 |

* cited by examiner

*Primary Examiner* — Brian J Sines
(74) *Attorney, Agent, or Firm* — Ulysses John Biffoni (57) ABSTRACT

An improved system for collecting, detecting, and classifying submicron-sized particles in a sample comprising an Integrated Virus Detection System (IVDS) of the type wherein the detecting means includes a differential mobility analyzer (DMA) and condensation particle counter (CPC), the improvement comprising positioning an aerosol collector or an electrostatic collector between the differential mobility analyzer and the condensation particle counter wherein submicron-sized particles from the environmental sample are collected for further analysis.

6 Claims, 7 Drawing Sheets

<image

Channel Particle Midpoint (nm)

Channel Particle Midpoint (nm)

VIRUS AND PARTICULATE SEPARATION FROM SOLUTION

GOVERNMENT INTEREST

The invention described herein may be manufactured, used and licensed by or for the U.S. Government.

FIELD OF THE INVENTION

The invention relates to the field of small particle separation and methods for their detection and identification.

BACKGROUND OF THE INVENTION

Detection and correct classification of nanometer sized viruses that include previously unknown, emerging or engineered strains, requires novel approaches and strategies. The current approaches based on identification via analysis of nucleic acids using PCR-based methods, gene chips and sequencing are effective in identifying known pathogens, however, development of novel approaches are needed to detect and classify unknown or engineered microbes of interest. Current methods are limited in their effectiveness and those microbes that are not sequenced can be invisible to these methods. One major issue with current approaches is that samples that contain mixtures and environmental components may interfere with the precise molecular biology processes. Thus, a real world sample that contains multiple viruses, various nanometer components of cells, and various salts and metals can pose a difficult prospect for current systems. Unknown viruses need to be isolated for further analysis, cloning, sequencing, and processing. It is difficult to have two unknown or many unknown viruses in a sample when trying to use current methods for analysis. A new method is needed that can detect, separate, isolate, and enhance nanometer sized particles viruses from real world samples.

The integrated virus detection system (IVDS) 100 is described in U.S. Pat. Nos. 6,051,189; 6,485,686; 6,491,872; and 7,250,138, all of which are incorporated by reference herein. The invention disclosed and claimed herein is an improvement thereof.

Figure 1:
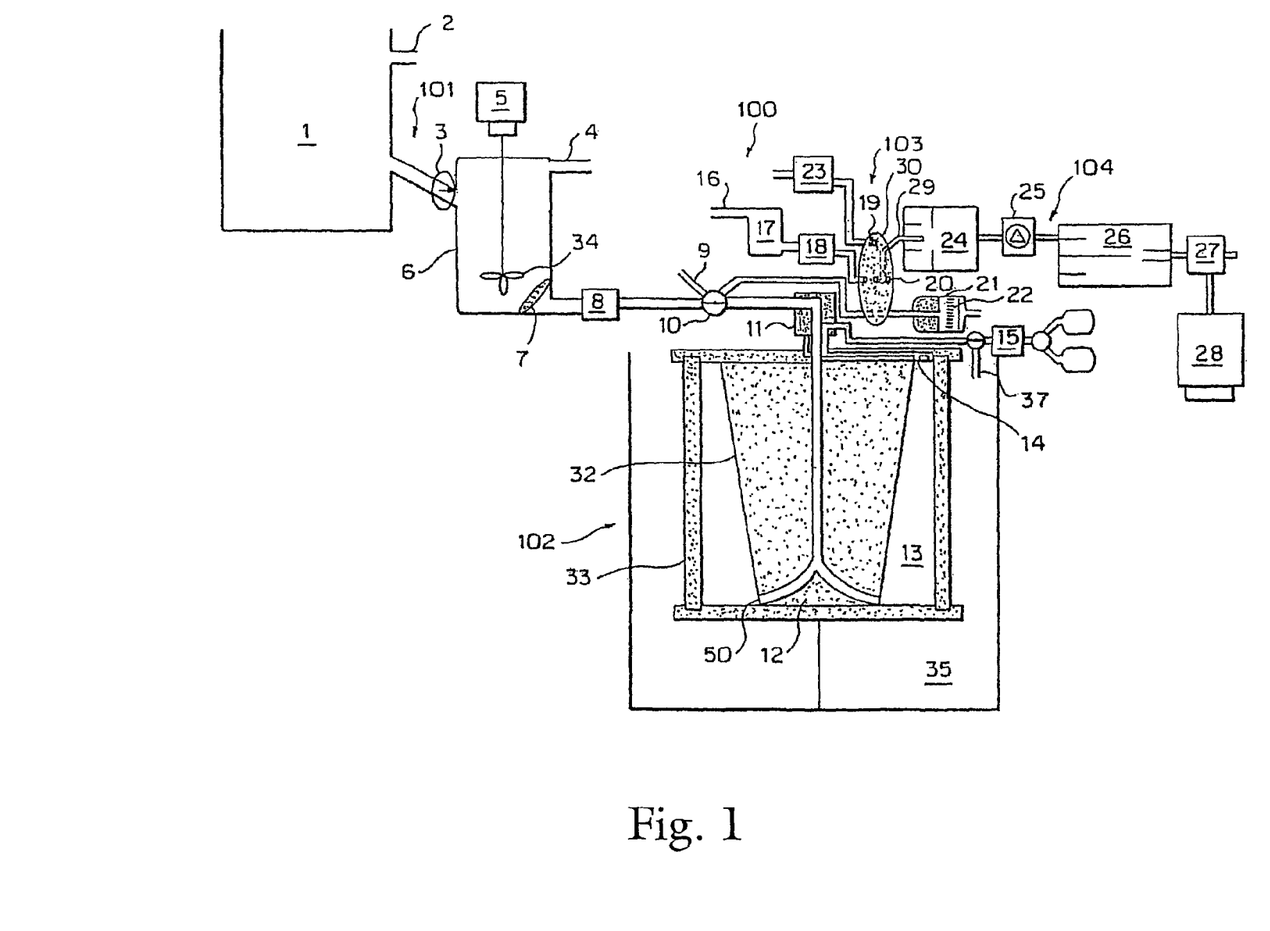

Referring now to FIG. 1, an integrated virus detection system (IVDS) 100 of the present invention is shown. The IVDS includes a collection stage 101, an extraction stage 102, a purification/concentration stage 103, and a detection stage 104. These four stages are herein further described.

In the collection stage 101, a collector 1 is used for aerosol or gaseous fluid sampling. In aerosol sampling, the collector 1 samples airborne particles having sizes which optimally carry viruses, preferably a size of 2-10 microns, and at collection rates of 1,000 liters/min of air. Collection of the submicron size virus particles in the collector 1 is facilitated by the fact that airborne viruses generally travel in or on aerosol particles which measure larger than a micron. In exceptional cases where the virus is not rafting on a supermicron fomite, the danger of transmission by inhalation is generally reduced because of the distribution of submicron particles in the atmosphere and the difficulty in capture by the lungs. The collector 1 has a water inlet 2 which is connected to a water source, such as tap water or other water purification system. The collector 1 scrubs the collected particles with the incoming water from the water inlet 2. Examples of the collector 1 are the U.S. Army's XM2 or the SPINCON collector made by Midwest Research Institute.

In many applications other than aerosol sampling, specimens possibly containing, for example, viruses are obtained without need for what would be considered a formal "collection stage", in particular when the specimen is already in liquid form. These include, for example, blood samples, obtained by ordinary means familiar in clinical settings, as well as other body fluids such as mucus, semen, feces, lymph, saliva, etc. Also in this category are situations involving sampling of bodies of water such as municipal water supplies, rivers and lakes, beverages, and high-purity water for microelectronics manufacture.

The collector 1 further has tubing 3 which connects the collector 1 to a holding tank 6 having a blender or homogenizer 5. The collector 1 has an aqueous stream output on the order of 1-10 ml/minute containing the scrubbed particles which is pumped through the tubing 3, which is preferably TEFLON or polysiloxane-coated to reduce adsorptive losses. The tubing 3 goes preferably to a one liter holding tank 6. Alternatively, the tubing 3 goes directly to the extraction stage 102.

In the holding tank 6, solids in the aqueous stream are broken up by using the homogenizer 5, or alternatively, by forcing the aqueous stream through an orifice. The homogenizer 5 has a bladed section 34. Surfactant or amphiphile is added at the inlet 4, which preferably is mixed with water prior to entry into the holding tank 6. The surfactant or amphiphile breaks down the structures in the aqueous stream. Preferably, the amphiphile has a low boiling point, which allows easy removal of the amphiphile in a later stage. Most preferred, the amphiphile is diethylene glycol monohexyl ether. Base is also preferably added to increase the pH of the homogenized liquid which tends to decrease aggregation. Examples of the homogenizer 5 are the Lightnin Closed Tank Model general purpose stirrer model G2S05R, available from Lightnin, a unit of General Signal of Avon, N.Y., catalog no. 869435, or the PC-controllable stirring motor, RE 162 analog, ID no. 8000700 and rotor-stator S 50 N-W 65 SK, ID no. 8005100 from IKA Works, Inc. of Cincinnati, Ohio, which serves as part 34.

In leaving the holding tank 6, the aqueous stream passes a screen filter 7 which regulates the output of the holding tank 6. The screen filter 7 is preferably 10 micron mesh and made of stainless steel or other corrosion-free material. A pump 8, which is designed for pumping liquids through the tank 6, draws the aqueous stream from the holding tank 6 and through the screen filter 7.

Beyond the pump 8, a three-position PC-controlled switch 10 is used to allow the discharge from pump 8 to flow into a centrifuge rotor 12 in a first position. To understand the function of the second and third positions of this switch, it is necessary to realize that after centrifugation, the gradient imprisoned in the rotor can be divided into two parts: the useful part which contains that range (or in some cases, those ranges) of densities in which the particles to be detected are expected to lie, and the remainder which will generally be discarded and not sent on to the next stage. Thus, for example, in the detection of viruses pathogenic to humans, this useful part could be that part of the gradient corresponding to densities of 1.175-1.46 g/ml, as discussed elsewhere herein; alternatively, a subset of this range could constitute the useful range if only certain viruses are being analyzed for.

Thus, the second position of switch 10 allows the useful part of the gradient to flow on to part 30 (in particular, to the first position of part 30, as discussed below), and the third position of the switch allows the discarded portion of the gradient from the rotor 12 to flow out through a port 9; if desired, port 9 can incorporate means to recycle density gradient material. In the first position, as the screen-filtered sample from the pump 8 travels past the switch 10, it enters into the extraction stage 102.

In the extraction stage 102, the aqueous stream enters a liquid-cooled coaxial seal 11. After passing the coaxial seal 11, the aqueous stream enters at the upper shaft of the rotor 12. The rotor 12 is a zonal ultracentrifuge rotor, such as a Beckman's CF-32 rotor or Z-60 rotor, which is inserted into and spun by a centrifuge 35, such as a Beckman Optima XL-100K Preparative Ultracentrifuge. For large sample volumes with small quantities of viruses, for example monitoring of bodies of water, such as drinking water sources, the present invention preferably uses continuous-flow density gradient ultracentrifugation, using for example the Beckman's CF-32 rotor. For other applications, ordinary zonal centrifugation is preferred with rotor 12 being a Beckman's Z-60 rotor. In a special seal and bearing assembly, fluid inlet and outlet streams access an annular space 13 between a core 32 and rotor wall 33 through the coaxial seal assembly 11 and via port 50. Density gradient solutions, sample liquid, and the displacement fluid are sequentially pumped into the annular space 13. Density gradient solutions are loaded from port 15 through inlet 14. From pump 8, sample liquid is added. A density gradient solution is any liquid which permit the separation of viruses, such as a sucrose or, preferably, cesium chloride solution.

In continuous flow operation, the virus-containing liquid stream is pumped in from the collection stage 101 and flows continuously over the density gradient in the rotor 12, and viruses sediment out of the stream, banding into the density gradient according to buoyant density. This pumping of sample into and out of the rotor 12 can be performed with the centrifuge spinning at high speed. The continuous stream allows a large volume of fluid to flow through the annular space 13, which permits virus material to be captured in the gradient, even with small concentrations of viruses in the fluid. In ordinary zonal operation (not continuous-flow), the sample does not flow continuously into the rotor for long periods of loading, but rather the entire sample volume, which must be less than the annular volume in the rotor, is loaded and enclosed in the rotor 12. The rotor volume is then closed off before acceleration to high speed. In either case, this is called the loading phase of the isopycnic banding separation. After loading and centrifuging to achieve banding, the virus-containing bands are recovered by displacing the bands sequentially, with lowest density bands exiting first and highest density last. As the density of each virus uniquely determines the position of that virus or particle in the exiting stream, the timing of the detection of specific virus particles provides particle density information.

A fresh gradient is loaded into the rotor 12 by pumping a low density fluid, containing no cesium chloride, into the rotor 12. As illustrated schematically by the presence of two fluid tanks and a mixing valve in part 15 of FIG. 1, a high density fluid, typically containing about 60% cesium chloride is mixed with the low density fluid at a variable high:low ratio, which via PC control increases with time until the loading is complete. The fluids pass through the fluid entry ports 14 at the top of the annular space 13. Concurrently, the rotor 12 is spinning at a low speed of about 4,000 rpm, with the speed being controlled by the timer control system in tandem with the fluid entry and displacement.

After the fresh gradient is loaded, the control system actuates valves which flow fluid through the rotor 12 in the opposite direction, pumping sample from the holding tank 6, through switch 10 (in the first position), through the bottom entry port 50, and upward through the annular space 13, entering at the bottom end and displacing fluid out at the top of the rotor 12 through 14 and out discharge port 37. After establishing flow reversal, the control system initiates and regulates the centifuge to a preferred rotational speed of about 60,000 rpm for a B-series rotor. In extremely dry environments, water exiting the centrifuge may be recycled back into the system by pumping it back into the collector 1 where it can be used for air scrubbing. At a rotational rate of 60,000 rpm and flow rate as high as 6 liters/hr, over 90% of all virus enters the gradient from the sample fluid stream, where it remains imprisoned. After on the order of 10-30 minutes of operation, which allows as much as 3 liters of sample fluid to pass through the rotor 12, the inflow and effluent flow are shut off, and the high-speed rotation continues for an additional 30 minutes to band the viruses. The viruses become banded in the gradient. The centrifuge controls are actuated by a timer-regulated control system, which is preferably a standard PC-computer interface.

In operation, sample liquid is introduced into the density gradient within the centrifuge rotor at the low-density end of the gradient, and each particle or molecule penetrates into the gradient at a rate that increases with the mass of the particle, and with the density. In the case of a protein molecule, the mass is much smaller than that of a virus by at least an order of magnitude, and the density is about the same as that of a relatively low-density virus. Accordingly, the rate of banding for proteins is much slower than for viruses. The centrifugation is run just long enough for the smallest virus particles of interest to have enough time to band to the desired resolution in the gradient. This is typically within about 1-5% of the equilibrium position. The proteins will then primarily be to the low-density side of their equilibrium positions, as they started on that side. Since the equilibrium position of most proteins in a gradient is nominally about 1.3 g/ml, at the end of this shortened operating time, most proteins are positioned considerably lower than 1.3. The proteins are at positions which are not collected, and not sent on to the next stage as they are outside of the "virus window". Accordingly, the density-gradient centrifugation step takes on some of the properties of a combined two-stage density-gradient/sedimentation coefficient separation.

Once the viruses are banded, the centrifuge is decelerated to low speed, and the gradient is recovered by pumping the dense fluid of preferably 60% CsCl from the gradient supply system 15 to the outer edge of the annular space 13 through 14. The dense fluid displaces the gradient, with low density bands exiting first followed by high density bands. After gradient removal, the high density material in the rotor 12 is displaced by low density fluid, which enters from the inner rim of the annular space 13 at point 50 and displaces the high density material from the outer edge of the annular space 13. The procedure is complete in a few minutes, and the cycle repeats again beginning with the loading of the density gradient at low speed.

Ultracentrifugation provides the advantages of desorption of viruses from fomites and universal capture of all catalogued and non-cataloged viruses, with high capture efficiencies of greater than 95%. Ultracentrifugation also is not dependent on biochemical reagents, and provides a high degree of virus separation from the background components. Additionally, density information of the viruses is provided by the ultracentrifugation, providing the y-coordinate in the Virus Window plot, discussed herein. The coaxial seal 11 is commercially available as a Beckman's Zone Assembly, part no. 334241. Examples of the centrifuge rotor are the U.S. Army's B-VII, B-IX and B-XVI, or preferably the Beckman Spinco CF-32 Ti Continuous Flow Rotor, or Beckman's Z-60 rotor for ordinary zonal centrifugation. For the centrifuge itself; the Beckman Optima XL-100K Preparative Ultracentrifuge is well-suited for all of these rotors.

The results of the extraction of the ultracentrifugation of the centrifuge rotor 12 are analyzed from biological background by means of a "Virus Window." The Virus Window is a density-size (.rho.-d) or density-sedimentation coefficient (.rho.-S) plot of biological components which are pathogenic to humans, with the x-axis showing either size d or sedimentation coefficient S, and the y-axis showing density .rho. Mammalian viruses are approximately between 1.175 and 1.46 gm/ml density and have a diameter between about 22 and 200 nanometers (or, alternatively rephrasing this size range, with sedimentation coefficient between 120 and 6,000 Svedberg units). The Virus Window is an extremely useful concept not only because it shows how viruses can be separated from other non-viral background, but also because the different virus families are substantially separable from each other. Within the Virus Window, each virus family is distinguished by a particular rectangle with little overlap between the 20 family rectangles. Accordingly, with a known density and size, the detected virus particle is pinpointed to its particular family in the Virus Window. In any case, particles with densities and sizes that both fall in the Virus Window ranges can, with high confidence, be presumed to be viruses; thus when counts are registered in the detector of the present invention, having previously been selected by centrifugation for density in the range of about 1.175 to 1.46, and further selected by the Differential Mobility Analyzer for size between about 22 and 200 nm, then it can be concluded with a high degree of confidence that these indicate the presence of viruses in the sample. Furthermore, this confidence level is further increased if the density and size fall into a particular region of the Virus Window known to correspond to a virus. Similarly, other particles of potential interest in detection—such as prions, other virus-like particles, and other natural or artificial particles, colloids, cell structures, or macromolecules—will frequently have unique positions in the density-size plot that may allow them to be separated from other components and thereby be detected in the present invention.

Although to a very large degree only pathogenic viruses fall within the Virus Window, other background components fall close to the Virus Window. These components are microsomes and similar sub-cellular structures. These components can be effectively eliminated by adding nonionic surfactant, such as diethylene glycol monohexyl ether, to the collection stage 101 exit stream at inlet 4. The surfactant solubilizes the microsomes and membrane fragments. As recovery of viable viruses is not necessary, release agents can be used. The release agents are preferably organic solvents and surfactants, more preferably amphiphiles, and most preferably low molecular weight amphiphiles such as diethylene glycol monohexyl ether. The release agents provide several useful effects. First, they act to break up and even dissolve cellular substructures, such as microsomes, ribosomes, lysosomes, peroxisomes, and mitochondria, which have sizes and densities similar to viruses and set the limit on the required resolution, in the case of detection of viruses. Second, upon dissolution of the lipid envelope with such agents, the increase in the virus density is significant (the density of the viral core, which is the virus minus its lipid envelope, is in general significantly higher than that of the enveloped virus). In the case of hepadnaviridae, for example, this may be from about 1.25 to 1.36. Both effects serve to further differentiate viruses from, particularly, microsomes in the Virus Window plot, the first by acting to eliminate the microsomes, and the second by increasing the difference in density between the viruses and the background microsomes. Third, release agents enhance the desorption of viruses from solid matter, which is particularly important in the detection of airborne viruses. Release agents can also break up aggregates of viruses, especially aggregates of encapsulated viruses. The present invention minimizes this aggregation problem in other ways besides the use of release agents. The centrifugation can be performed without pelleting. Consequently, buoyant density, and thus isopycnic banding, is not greatly affected by aggregation under these circumstances. (Indeed, banding times are favorably reduced in the case of aggregation, and techniques can be applied that take advantage of this, within the broad context of the present invention). Any aggregation will generally produce only a small shift in, and/or broadening of, resulting virus bands. The portion of this exiting stream that contains the Virus Window is pumped to the purification stage 103 with the position of a particle along this stream giving the density of that particle. The useful part of the stream, in the case of general virus detection where the range 1.175-1.46 passed to the next stage, is in the preferred embodiment on the order of about 10 ml; thus, this stage does not effect a large increase in virus concentration, though it does effect a very large increase in the concentration of viruses relative to other non-viral components.

Although feasible, a separate centrifugation to separate particles by sedimentation coefficient for Virus Window x-coordinate information is not necessary. A Differential Mobility Analyzer (DMA) 26, which as described below, provides rapid analysis of particle size. Additionally, separation of viruses from soluble proteins can also be done in the purification stage 103. An even further separation of proteins, and other macromolecules smaller than viruses, from viruses can also be done by tuning the supersaturation in a condensation particle counter so as to not detect macromolecules as small as proteins. The centrifuge dimension and rotor speed for optimal centrifugation can be calculated. Optimal times are preferably thirty minutes or less and resolutions are preferably 0.02 density units (0.02 gm/ml) or better.

The sample fluid passes from the extraction stage 102 into the purification stage 103. Typically, this could be in the form of 15 pulses, each on the order of 1-10 ml in volume, and each corresponding to a density slice with a width on the order of 0.02 gm/ml. In the purification stage 103, an ultrafiltration (UF) membrane 22 separates the viruses from soluble proteins (removing the need for a second, sedimentation rate centrifugation in the previous extraction stage 102), and concentrates particles with sizes greater than the pore size into a very small volume of liquid; additionally, in this stage soluble salts, including those from the sample as well as the density gradient material (e.g., cesium chloride), are greatly reduced in concentration. The UF membrane 22 may be Millipore's VIRESOLVE Membrane, an AMICON P membrane, or preferably a Pall FILTRON OMEGA Series membrane with a 1,000,000 molecular weight cutoff. The water permeability of the UF membrane 22 is on the order of 0.01 ml/cm$^2$-sec-psi, so that a membrane area of 0.1 cm$^2$ yields a flux of order 6 ml/min at 100 psig transmembrane pressure. The UF membrane 22 is incorporated into a housing which is designed to allow flow rates on the order of 0.1-20 m/min during ultrafiltration, which results in loading of the filter with particles larger than about 15 nm (which includes all virus particles), after which the particles are confined within a small front-face-side collection volume. A small-volume filtration filter holder 21, such as Schleicher & Schuell's SELECTRON, is used to hold the UF membrane 22. More preferably, a filter holder with a design like that of the SELECTRON, but made out of an alternative material which does not degrade electrolytically under high voltage, is used.

A four-way positioner 30 in the purification stage 103 allows automated processing of particles in the UF membrane 22. The positioner 30 is driven by a computer-controlled motor which positions the filter holder in one of four ports.

In the first position, the positioner 30 positions the UF membrane 22 to accept the sample flow outputted from the extraction stage 102. Each 0.02 gm/ml density slice from the output of the extraction stage 102 is, after passing through switch 10 in the second position, loaded through the UF membrane 22 in less than about 2 minutes; alternatively, larger density slices can be ultrafiltered, requiring appropriately longer times. A standard 0.2 micron poresize filter (such as available from Corning Costar) is preferably incorporated in the connection between the output from 102 and the input to 103, in order to remove any remaining particles greater than about 200 nm in size.

When the positioner 30 is switched to the second position, a valve closes off the sample flow and CsCl-free water from pump 18 out of tank 17 which has an inlet 16 is passed across the UF membrane 22 using on the order of 5 ml of water with a flux time of order 1 minute. This reduces the 30% CsCl aqueous solution surrounding the particles to less than 100 ppm CsCl, and allows recovery of the CsCl for recycling. Additionally, the amphiphile, viscosity additives and buffer components are reduced in the UF membrane 22. More preferably, ammonium acetate solution, with on the order of 20 mM concentration in water, is used for this operation, preparing the liquid for downstream detector stage operation.

On switching the positioner 30 to the third position 19, the pure water (or ammonium acetate solution) is shut off, and a final ultrafiltration is performed in order to reduce the volume of liquid on the retentate side of the membrane, thereby greatly increasing the concentration of viruses and reducing the volume of liquid to the small quantities required for operation of the detection stage 104; the filtrate in this step passes out through port 23. More precisely, the UF stage 103 is integrated with the electrospray assembly 24 of the detection stage 104 by a punctured disk fitting. The fitting has a 150 micron hole drilled through a tubular stub in its center. When positioner 30 is in the third position, this hole allows the filtrate to pass out through port 23. When the positioner 30 is in the fourth position, the inlet end of the electrospray capillary 29 (the end opposite the spray tip) is inserted into this 150 micron hole. This fits in a piston-like manner into the stainless steel cylinder of the SELECTRON (or SELECTRON-like) filter holder. The cylinder slides over the steel disk, and is positioned with a gap between the steel disk and the ultrafilter surface on the order of 100 microns.

In the fourth position 20, in accordance with the above, the UF membrane 22 is positioned for entry of the virus containing retentate into an electrospray capillary 29 of the detection stage 104. (Alternatively, instead of fluid passing directly from the purification stage 103 to the electrospray, an intermediate component may be used to accomplish a further purification and/or concentration). A platinum wire may be run from the voltage source of the electrospray unit 24 to the interior of the liquid inside the volume on the retentate side of the UF membrane, in order to establish a current return for the electrospray operation.

The detection stage 104 accomplishes several functions, which include a final purification, an individual virus particle count and a size determination of the detected particles. The detection stage 104 includes three major components, an electrospray assembly (ES) 24, a Differential Mobility Analyzer (DMA) 26 and a Condensation Nucleus Counter (CNC) 27, which is alternatively called a Condensation Particle Counter (CPC). The components may be commercially obtained individually from TSI, Inc. of St. Paul, Minn. The Condensation Nucleus Counter 27 and Differential Mobility Analyzer 26 units are also available commercially from TSI as a single integrated unit, which can be accompanied by an IBM PC with associated software. This allows for an inexpensive set up compared to a mass spectrometer. The detection stage 104 can conduct measurements concurrently with the collector 1 obtaining the next cycle's collection.

Passing from the purification stage 103, the retentate enters the detection stage 104 at the inlet of the electrospray capillary 29 of the electrospray assembly 24 in the fourth position of the positioner 30. Entry into the electrospray capillary 29 is done without passing the retentate through piping, which might cause sample losses. The electrospray capillary 29 is on the order of 25 cm in length, and the inlet of the electrospray capillary 29 is positioned to the small front-face-side collection volume of the UF membrane 22, as described above. The electrospray capillary 29 is then positioned to sample liquid from the retentate-side of the filter and the sample liquid enters the electrospray assembly 24.

In the electrospray assembly 24, the liquid sample solution is passed into an orifice or "jet" of 50 micron diameter, and droplets are ejected under the influence of an electric field. The droplets are typically between 0.1 and 0.3 microns in size, with a fairly narrow size distribution. At a droplet size of 0.3 micron, sampling rates are 50 nl/min (50 nanoliters/minute), allowing the electrospray assembly 24 to spray the collection volume in on the order of 20 minutes per microliter.

From the electrospray assembly 24, the sample passes to a charge neutralizer 25. The charge on the droplets is then rapidly recovered using an ionizing atmosphere to prevent Rayleigh disintegration. The neutralized ES droplets are then dried in flight, leaving the target virus molecules and/or dried residue of soluble impurities. From the charge neutralizer 25, the target virus molecules and/or dried residue enters the Differential Mobility Analyzer (DMA) 26.

The Differential Mobility Analyzer 26 uses electrophoretic mobility of aerosol particles to classify the particles by size, using the inverse relationship between the mobility of a particle to its size. In the Differential Mobility Analyzer 26, particles are carried by an air stream at a set velocity through an electric field created by a charged rod. If the particle is singly and positively charged, it experiences an electrostatic attraction to the rod, which competes with the inertial force of the flow. When the electrophoretic mobility falls in a certain range, the particles pass through a narrow exit port at the end of the charged rod. The particle size range, which is generally 0.01 to 1 micron, is divided into 147 size channels. The entire range is automatically scanned in 1 to 10 minutes, generally 3 minutes. The Differential Mobility Analyzer 26 has only a possible 3% instrumental error for virus size determination. Additionally, there is a possible size increase due to the covering of the virus particle with impurity residue, which at an impurity level of 100 ppm, a typical 40 nm virus has a possible error of up to about 2% in effective size. If the impurity levels are less than 20 ppm, the error becomes smaller than 1%.

When the primary droplets from the electrospray assembly 24 are 0.3 micron, a 1 ppm soluble impurity creates a 3 nm residue particle, and a 125 ppm soluble impurity creates a 15 nm particle. Particles which are 15 nm in diameter can be separated in the Differential Mobility Analyzer 26 from viruses which are at least 22 nm in diameter. Accordingly, soluble impurities must be reduced to less than 100 ppm (0.01%) to avoid background interference with virus signals.

Detection of proteins at levels of $10^{11}$-$10^{12}$ molecules/ml indicates that a sensitivity level for viruses of $10^{10}$ particles/ml can be achieved, and possibly $10^9$ particles/ml, particularly by combining the Differential Mobility Analyzer 26 selection with an adjustment of the Kelvin radius of approximately 10 nm. Impurities of 1 ppm yields a 3 nm residue particle which can overlap protein sizes. Impurity levels of 100 ppm or less are acceptable in the detection of viruses, since viruses are several times larger than proteins. Sensitivities of $10^{10}$ molecules/ml and possibly $10^9$ molecules/ml are projected based on documented results using proteins. In one of the Examples given below, detection of $10^{12}$ pfu/ml (a pfu is a plaque-forming unit) was easily accomplished even after dilution by a factor of 128, demonstrating detection at a level of $10^{10}$ pfu/ml.

The Differential Mobility Analyzer 26 validates against false positives by changing the dilution and seeing whether the particle size also changes. Additionally, the Differential Mobility Analyzer 26 can be used to provide another layer of protection against interference from impurities up to the 100 ppm level. The level of $10^{10}$ molecules/ml corresponds to $2\times10^7$ viruses in a 2 microliter collection volume of the purification stage 103, and $10^9$ molecules/ml corresponds to $2\times10^6$ viruses. At a collection volume of $10^7$ viruses of the present invention, or 20 minutes of XM2 sampling, 20,000 liters (20 m$^3$) of air are sampled. Accordingly, the sensitivity of the present invention is on the order of 500 viruses per liter of air. With impurity levels of 100 ppm or less, virus size can be determined by the Differential Mobility Analyzer 26 to within about 4%. The detection stage requires on the order of 5 to 40 minutes, including Differential Mobility Analyzer 26 size determination, and can be preformed concurrently with centrifugation for a subsequent cycle.

From the Differential Mobility Analyzer 26, the sample enters the Condensation Nucleus Counter 27, which uses a nucleation effect. The aerosol sample enters and passes through a heated conduit having an atmosphere which is saturated in butanol. The sample is routed into a cooled condenser, where butanol vapor condenses onto the sample particles, which act as nuclei. The saturation is regulated so that no condensation occurs on the nuclei below a critical size, which limits false background counts to less than 0.01 particle/ml. With nucleating particles, condensed droplets grow to micron size and are optically detected using a 780 nm laser diode with photodetector. Provided that the level of impurities is low enough that the residue particles are below the threshold of detection by the Condensation Nucleus Counter 27, and/or are separated from the target molecules by size, then only the target molecules will be registered with the Condensation Nucleus Counter 27. As the nucleation of droplets does not depend on surface characteristics of the particles, butanol saturation can be adjusted for a critical size of 0.01 micron radius which minimizes background counts from proteins and other soluble impurities. Response times for step changes in concentration are less than 20 seconds, and operation of all components is in the temperature range from 10° C. to 38° C. Supersaturation tuning for a 10 nm Kelvin radius threshold in the Condensation Nucleus Counter 27 can be used to cancel the detection of non-viral impurities, including proteins, provided they are below about 100 ppm.

The ultrafiltration stage has an output volumetric rate which is very well suited for input into the ES-DMA-CNC particle counter, which addresses the strict requirements and narrow range of operating parameters for the ES-DMA-CNC unit. In recognizing the high value of this molecule-counting and molecule-sizing ES-DMA-CNC unit, ultrafiltration provides excellent samples for the purification/concentration stage prior to this detector. The ES-DMA-CNC combination allows particles to be sized and permits improved sensitivity by an order of magnitude over a DMA-CNC combination. Protein concentrations of 10 mg/ml, or $10^{11}$-$10^{12}$ molecules/ml, can be detected and sized.

The system is controlled by a computer 28. When data collection and instrument control are handled by the same computer, the computer may vary the mode of operation in response to virus detection. Initially, before viruses have been detected, the system places the entire 300 ml of density gradient from the extraction stage 102 through the UF membrane 22 to scan all virus sizes from 22 to 200 nm. Alternatively, the Differential Mobility Analyzer 26 is by-passed entirely, provided that non-viral concentrations are low enough that tuning of the Kelvin radius in the Condensation Nucleus Counter 27 is sufficient to reduce background. Once viruses are detected, the Differential Mobility Analyzer 26 indicates the sizes of the viruses detected. The computer can then trigger the output of the extraction stage 102 to be sampled piecewise in the purification stage 103. By breaking the range of virus densities, which is about 0.3 gm/ml into 10 or 15 slices, the density of the detected virus is within about 0.02-0.03 gm/ml, which is sufficient to narrow most viruses down to a single family. Following this, the region in the centrifuge output stream surrounding this density can be divided still finer, to provide better accuracy on the viral density. Through data base comparison, the system identifies the viral families from the measured densities and sizes, and provides output of detected viruses by density, size, concentration, apparent changes in concentration over time, and if desired, audible and/or visual alarms in the presence of detected viruses. Being automated, the instant invention can run continuously for long periods of time without an operator. In addition to making continuous virus monitoring possible at a large number of sites simultaneously without the need for scores of virologists, the automation afforded by the present invention also limits the risks of viral infection of technicians.

Other physical means of separating viruses and other particles from background and/or enriching their concentration, which are substantially equivalent in their effect to the purification and concentration means discussed above, and which can be applied in addition to or in substitution for these means without departing from the spirit or scope of the present invention, include capillary electrophoresis (purification and concentration enrichment), sedimentation-rate centrifugation (primarily purification), hydroextraction (mainly concentration), dialysis (purification and concentration), organic/inorganic flocculation (purification and concentration), and capillary chromatography, which can size-exclusion, hydrophobic interaction, or ion-exchange chromatography (purification and concentration).

OBJECTS OF THE INVENTION

The invention has as its main object the separation and identification of small particles, as for example, viruses.

The invention has as a further object the collection and separation of various submicron or nanosized particles.

These and other objects of the present invention will become apparent from a reading of the specification taken in conjunction with the enclosed drawings.

BRIEF SUMMARY OF THE INVENTION

Integrated virus detection system (IVDS) has been used to analyze viruses in various real world matrices including air, water, soil, sand, plant and animal matter, and numerous other situations that call for the detection of known or unknown viruses. The IVDS device and process also provides a means to separate nanometer particles by size, within 4 nm resolution power. In a single sample, several sized particles can be separated and characterized based on their differential mobility. The system has the potential to be used as a basis for isolating and enriching an individual virus from mixtures of viruses or biological particulates.

Figure 2:
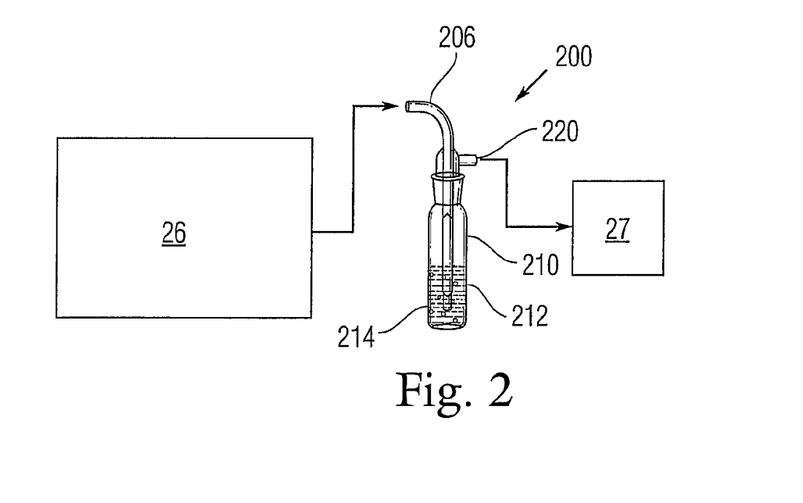

As depicted in FIG. 2, the inventor has improved the IVDS 100 by adapting it to provide an Aerosol Collector (AC) 200 between the DMA 26 and the CPC 27. The aerosol collector (AC) 200 will be described in detail below. This improvement permits specific viruses to be collected after being separated by the DMA 26. For example, if the DMA 26 has been set to separate MS2 virus at 24 nm, the MS2 can then be collected in the aerosol collector 200 as part of the IVDS system. The collected sample can then be further analyzed by the IVDS before entering the CPC 27, or it can be subject to further laboratory analysis such as by polymerase chain reaction (PCR).

The Differential Mobility Analyzer 26 is a component/device in the IVDS system which uses the electrophoretic mobility of aerosol particles to classify particles by size, using the inverse relationship between the mobility of a particle to its size. In the Differential Mobility Analyzer 26, particles are carried by an air stream at a set velocity through an electric field created by a charged rod. If the particle is singly and positively charged, it experiences an electrostatic attraction to the rod, which competes with the inertial force of the flow. When the electrophoretic mobility falls in a certain range, the particles pass through a narrow exit port at the end of the charged rod. The particle size range, which is generally 0.01 to 1 micron, is divided into 147 size channels. The entire range is automatically scanned in 1 to 10 minutes, generally 3 minutes.

The condensation nucleus counter or (Condensation Particle Counter) 27 is a device in the IVDS which uses a nucleation effect. An aerosol sample enters and passes through a heated conduit having an atmosphere which is saturated in butanol. The sample is routed into a cooled condenser, where butanol vapor condenses onto the sample particles, which act as nuclei. The saturation is regulated so that no condensation occurs on the nuclei below a critical size, which limits false background counts to less than 0.01 particle/ml. With nucleating particles, condensed droplets grow to micron size and are optically detected using a 780 non-laser diode with photodetector. Provided that the level of impurities is low enough that the residue particles are below the threshold of detection by the Condensation Nucleus Counter 27, and/or are separated from the target molecules by size, then only the larger molecules will be registered with the Condensation Nucleus Counter 27. As the nucleation of droplets does not depend on surface characteristics of the particles, butanol saturation can be adjusted for a critical size of 0.01 micron radius which minimizes background counts from proteins and other soluble impurities.

The IVDS (Integrated Virus Detection System) has therefore now been adapted to allow an aerosol collector 200 to be placed in line between the Differential Mobility Analyzer (DMA) 26 and Condensation Particle Counter (CPC) 27. The Differential Mobility Analyzer 26 uses electrophoretic mobility of aerosol particles to classify the particles by size using the inverse relationship between the mobility of a particle to its size. From the DMA the sample enters the Condensation Nucleus Counter, herein referred to as the Condensation Particle Counter (CPC) 27. The CPC 27 uses a nucleation effect wherein the aerosol sample enters and passes through a heated conduit having an atmosphere saturated in butanol, wherein the butanol vapor condenses onto the sample particles to act as a nuclei.

In addition, as depicted in FIG. 6, the inventor has also made further improvements in the IVDS 100 by incorporating an Electrostatic Collector (EC) 250 in line between the Differential Mobility Analyzer (DMA) 26 and Condensation Particle Counter (CPC) 27. The Electrostatic Collector 250 is used to sample an aerosol that has been conditioned and positively charged. The Electrostatic Collector (EC) 250 consists primarily of a grounded 258 cylindrical sampling chamber 252 with an electrode 254 and an insulator 256 at the bottom of the chamber 252. The Electrostatic Collector 250 has an inlet 260 and an outlet 262. There is also a substrate 264, wherein the aerosol flow focuses particles 270 onto substrate 264. Particles 270 in the air flow enter the inlet 260 into interior of chamber 252 and, if not collected on substrate 264, leave outlet 262 to enter into the Condensation Particle counter 27.

Several experiments were performed to determine the feasibility of actual separation and collection of sample virus and polystyrene latex (PSL) particles. The separation of particles is performed in the IVDS system due to its ability to monitor and control the parameters of differential mobility in the DMA 26 while analyzing samples. Several methods including filter capture, electrostatic collection and aerosol collection were examined to collect the separated particles for further analysis.

BRIEF DESCRIPTION OF THE DRAWINGS

FIG. 1 is a schematic view of the Integrated Virus Detection System (IVDS) which is improved by the present invention.

FIG. 2 is a schematic view wherein the IVDS is adapted to accommodate an Aerosol Collector (AC) between the DMA and the CPC.

FIG. 3 shows an initial scan of stock MS2 virus solution after use of the AC.

FIG. 4 shows MS2 collected in 80 ml buffer wherein a small amount of MS2 remains in the scan.

FIG. 5 shows in a collected and ultrafiltered sample to better define an MS2 peak at 24 nm.

FIG. 6 shows an Electrostatic Collector (EC) in line between the DMA and CPC of the IVDS.

FIG. 7 shows a test run using a MS2 stock solution with an Electrostatic Collector between the DMA and CPC.

FIG. 8 shows a small peak for MS2 after electrostatic collection.

FIG. 9 shows polystyrene latex particles collected with the electrostatic collector.

FIG. 10 shows the result of redispersing the sample from FIG. 9.

DESCRIPTION OF THE INVENTION

IVDS Differential Mobility Separation

The IVDS analyzes viruses and other nanometer sized materials by separating particles according to their mobility in an electric field. The electrical mobility of a particle is a function of its size and the number of charges in contains. For particles in the size range of a few nanometers the electric charge that a particle will acquire is limited to a single elemental charge that is forced by the passage of the aerosol stream past an ionization module. Thus, the mobility of the charged particles in an electric field will be limited to their size only.

The differential mobility analyzer (DMA) 26 of the IVDS is comprised of a cylinder with a central rod. A controlled DC potential differential (0-10,000 VDC) is applied between the cylinder and the central rod. By controlling this potential, only particles with very narrow electrical mobility (size) are allowed to enter the opening slit at the bottom of the cylinder and exit the DMA. Due to the computer controlled timing software, the particles exiting the DMA are of a known electrical mobility, and can then be counted, sized, or collected.

Another possible collection area in the IVDS system is the exhaust from the condensation particle counter (CPC) 27.

Particle capture can be monitored with the IVDS computer controlled interface. The particle display is shown in near real time and allows control of the parameters for the flows in the instrument.

Aerosol Collection

The apparatus 200 in the center of FIG. 2 is an All Glass Impinger AGI-30. This device is used in sampling microbial aerosols of various types. The AGI-30 aerosol collector 200 is an all glass device that operates in the following manner. An aerosol flow enters the collector 200 through a curved inlet tube, generally to simulate a human nasal passage, thereby flowing into a container 210. The container 210 is partially filled with a liquid 212 and the aerosol is passed into the liquid 212. In this application, 80 ml of ammonium acetate buffer was used as the liquid 212 in the container 210. Excess aerosol gas 214 bubbles through the liquid 212 and then passes out of the container 210 at outlet 220. Thus, the aerosol enters the container 210 through a curved inlet tube 206 and then passes/bubbles through a liquid 212 and then exits the container 210 at outlet 220. In some applications a vacuum is used to facilitate microbial collection. In this application, the aerosol exits the IVDS device DMA 26 and is fed into the aerosol collector 200 under pressure, usually 2 psi at a flow rate of 2 liters/minute. Collection of microbes occurs as the bubbles pass through the liquid 212 in the container 210. The microbes are deposited in the liquid 212 as the bubbles pass through. In the case of small viruses, the aerosol flow rate, the size of the bubbles, and the linger time of the bubbles in the liquid are important variables.

The IVDS was adapted to allow an AGI-30 aerosol collector 200 to be placed in line between the DMA 26 and the CPC 27 as shown in FIG. 2. The collector was filled to 80 ml with a 20 mM ammonium acetate buffer with 50 mM isopropyl alcohol. The IVDS was set to scan at 20-30 nm for 30 sec and return. The scan was repeated 60 times for a total time of ~30 min sampling time. In this experiment tests were conducted for MS2 bacteriophage (virus that lives on bacteria).

Figure 3:
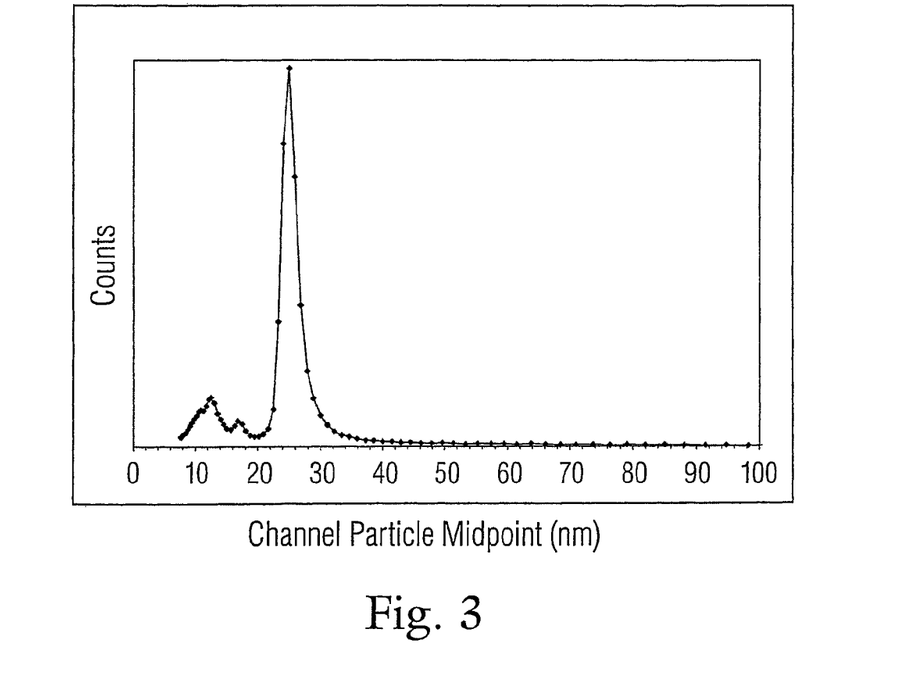

FIG. 3 is a graph showing a standard solution that contains MS2. It has a nominal size of 23 nanometers. MS2 is used as a size standard for calibration of the instrument and as a standard virus particle for routine laboratory use. In the graph the sample was diluted from a primary solution to 1:20 in 50 mM isopropyl alcohol (IPA) in 20 mM ammonium acetate (AA) buffer. This average number of scans represents the number of separate times the IVDS instrument counted the MS2 in the sample, averaged over a number of different counting periods. The caption on the horizontal axis represents the size of the particles in nanometers—in this case the particle midpoints. The IPA was added to reduce the surface tension in the water.

Figure 4:
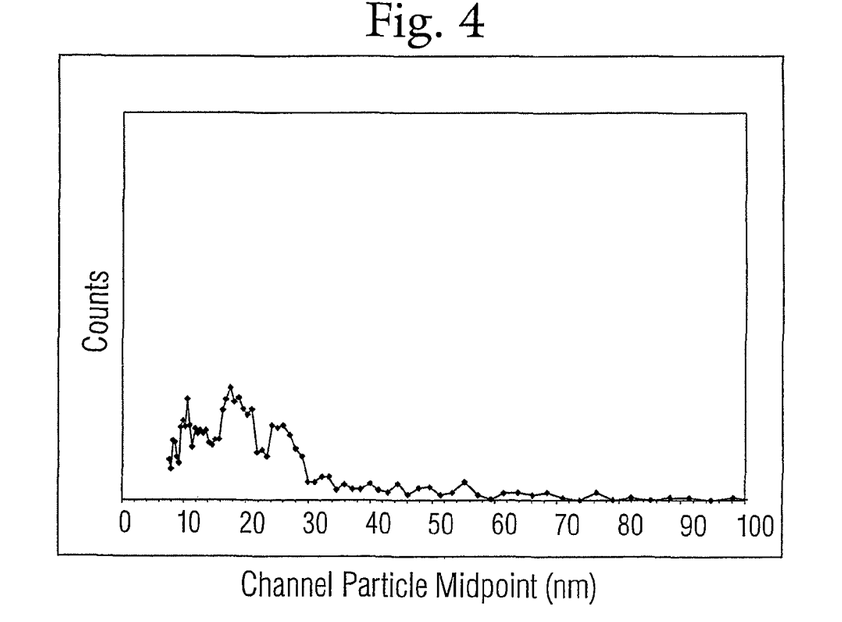

The initial scan of the stock solution is shown in FIG. 3. The MS2 has a well defined peak at 24 nm. After collection in the aerosol collector 200, the sample collected can be further tested or evaluated by other means, for example, by PCR. After collection in the aerosol collector 200, the 80 ml sample was again analyzed with the IVDS. As shown in FIG. 4, the collected sample contained a small amount (relative to the original sample amount) of MS2 in the scan. However, the data of FIG. 4 confirms that the MS2 has been collected. The 80 ml sample was then ultrafiltered to concentrate the volume down to 1.5 ml. The ultrafiltered scan, shown in FIG. 5, shows a better defined MS2 peak at 24 nm, again confirming that the MS2 has been collected from the sample.

FIG. 4 shows the particle counts for an unfiltered sample taken directly from the AGI-30 aerosol collector 200. The caption at the top is record keeping information and in this case identifies that the sample was an MS2 sample collected in 50 mM IPA in AA buffer. The sample was collected while the liquid was stirred. It is for an average of 6 scans (counting periods by the IVDS).

Figure 5:
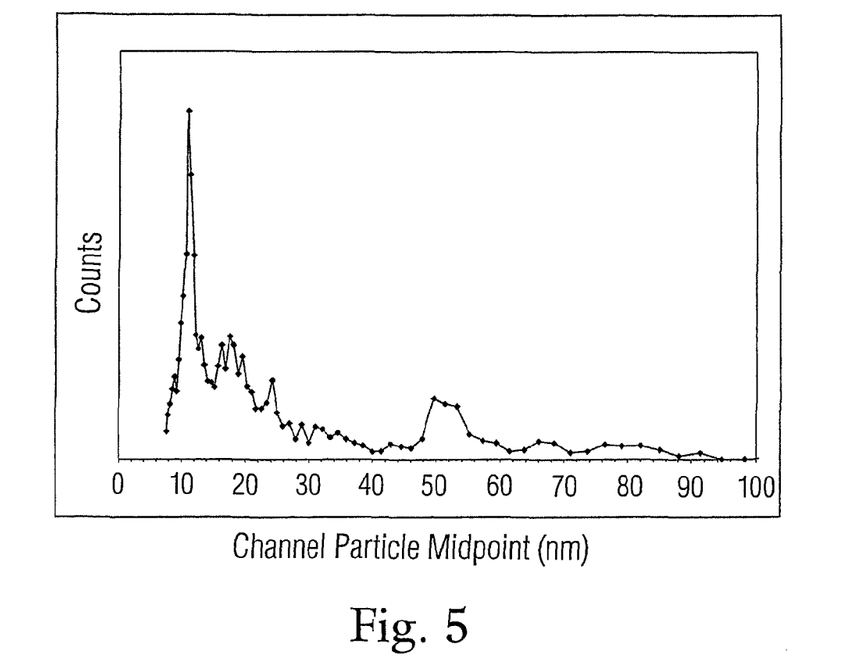

FIG. 5 represents the particle counts for the solution in FIG. 4 that is reduced or concentrated from 80 ml to 1.6 ml by use of ultra filtration (UF). The UF was a 600K Dalton filter. The numbers are for an average after six counting periods.

Electrostatic Collection

Figure 6:
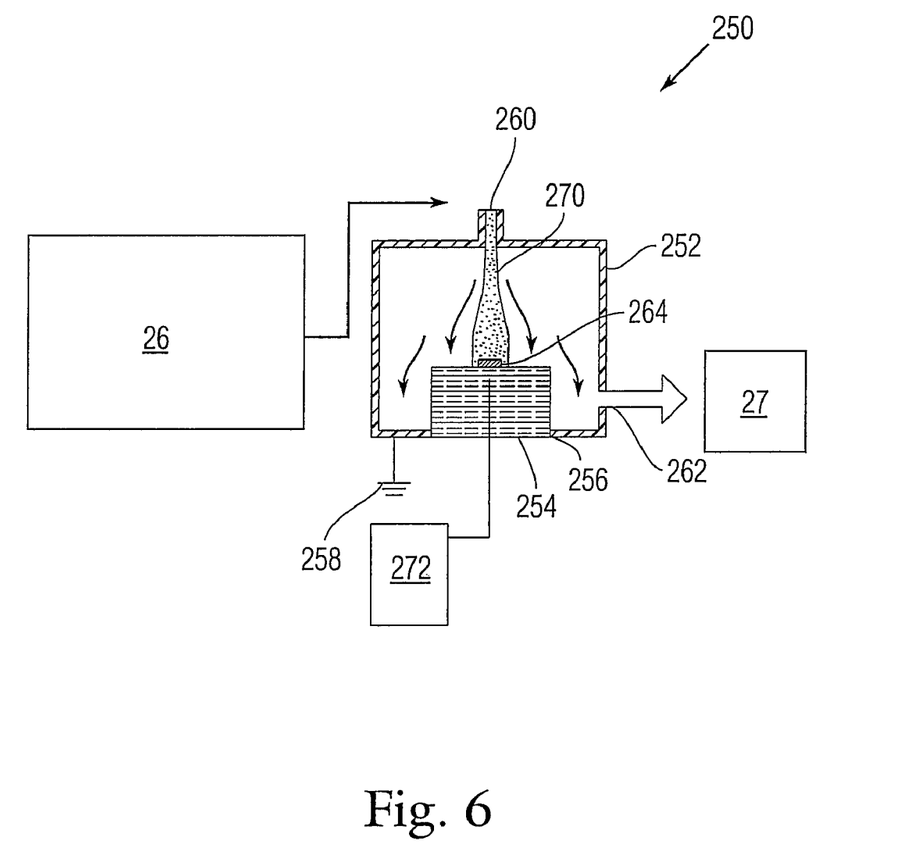

With reference to FIG. 6, the electrostatic collector 250 is used to sample an aerosol that has been conditioned and positively charged. The aerosol stream in the IVDS is positively charged by passing by an ionizing source, i.e., the DMA 26. The collector consists primarily of a grounded 258 cylindrical sampling chamber 252 with an electrode 254 at the bottom of the chamber 252. A negative potential of up to 10,000 volts can be set on the electrode 254. A pump (not shown) is used to draw aerosol 270 into the chamber through inlet 260. In operation, a sample substrate 264 is fixed to the electrode 254 with adhesive tape or other means. The sampler is then run at a fixed flowrate and voltage. The electric field between the grounded chamber 252 and the electrode 254 focuses particles onto the substrate 264. The substrate 264 can be any electrically conductive material, for example, stainless steel foil was used for some tests. The substrate 264 can then be removed after a period of time and the particles further analyzed. For example, the particles collected can be redispersed into buffer solution and then analyzed with the IVDS. The arrows within the chamber indicate air flow.

Figure 7:
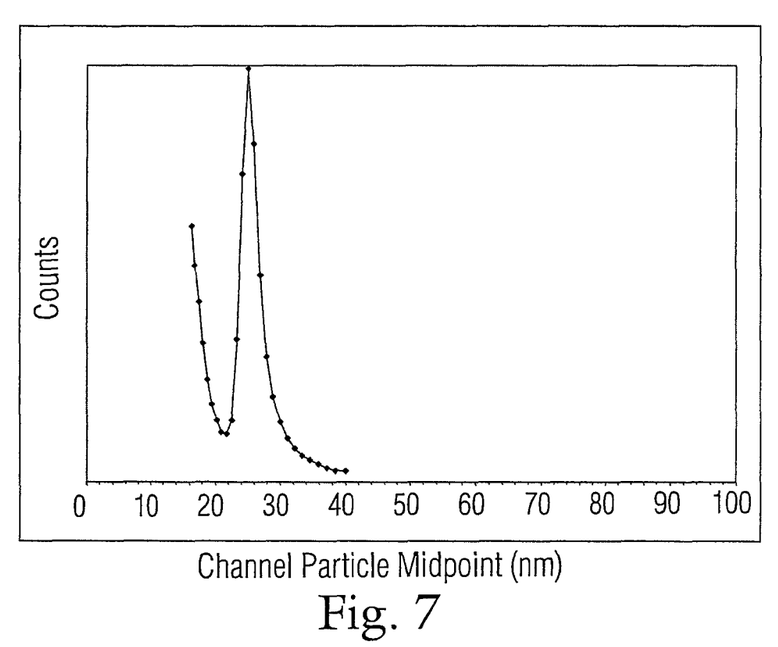

A sample of MS2 (D3), FIG. 7, was run on the IVDS with the electrostatic collector 250 between the DMA 26 and the CPC 27. The parameters for the collector are listed in Table 1. As the collector is in line with the DMA 26 and CPC 27, shown in FIG. 6, the flow is provided by the IVDS hardware.

TABLE 1

| MS2 electrostatic collector parameters | |
|---|---|
| Flow | 1 lpm |
| Volts | 9 kV |
| Time | 150 min |
| Foil (substrate) | Stainless steel, 0.003" × 0.375" dia. |
| IVDS scan | 16 to 40 nm/30 sec |

Figure 8:
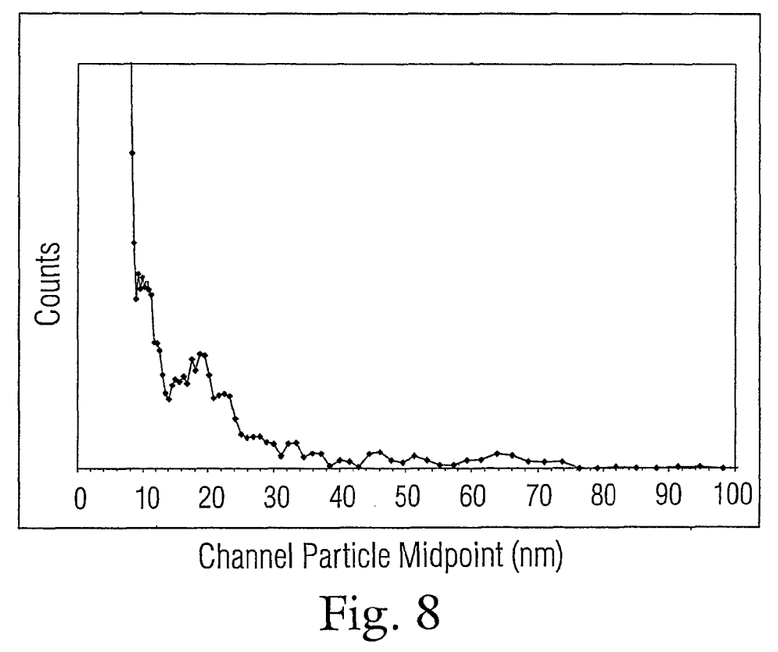

After washing the stainless steel disk with buffer solution, the sample was analyzed with the IVDS. As shown in FIG. 8, there is a small peak for MS2 after collection; confirming the collection of the MS2 from the sample.

Polystyrene Collection

Figure 9:
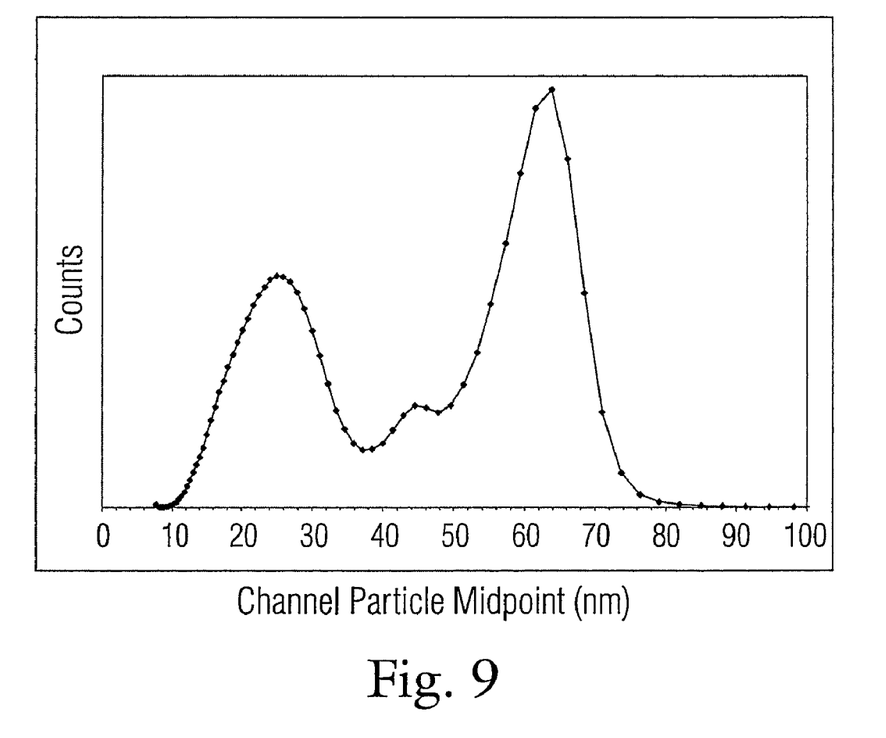

A sample of mixed polystyrene latex (PSL) particles, 30 nm and 70 nm, were also collected with the electrostatic collector. The results of a 30 nm 70 nm PSL stock mixture is shown in FIG. 9.

Figure 10:
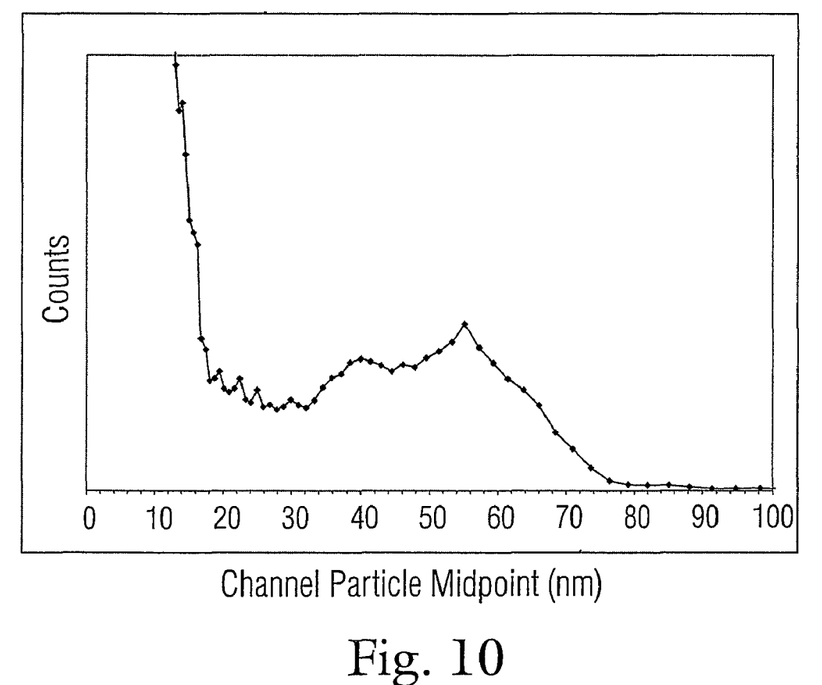

Table 2 shows the collection parameters for the PSL particles. The sample was redispersed in buffer solution for IVDS analysis. FIG. 10 shows the IVDS analysis of the collected sample as for example, 30 nm 70 nm electrostatic collection.

TABLE 2

PSL electrostatic collector parameters

| | |
|---|---|
| Flow | 1 lpm |
| Volts | 9 kV |
| Time | 950 min |
| Foil (substrate) | Stainless steel, 0.003" × 0.375" dia. |
| IVDS scan | 7 to 280 nm/120 sec |

CONCLUSION

The invention can be described as being an improved system for collecting, detecting and classifying submicron-sized particles in a mixture, comprising an Integrated Virus Detection System (IVDS) which has been modified by inserting an aerosol collecting means or an electrostatic collecting means between the Differential Mobility Analyzer (DMA) and the Condensation Particle Counter (CPA), wherein submicron-sized particles from the environment can be detected, separated, sized and identified. The aerosol collecting means is an Aerosol Collector and wherein the electrostatic collecting means is an Electrostatic Collector. More specifically, wherein the Aerosol Collector has a curved inlet attached to a container, allowing aerosol bubbles to pass through a liquid in a container and then exit the container, and wherein the Electrostatic Collector has a grounded cylindrical sampling chamber with an electrode at the bottom, a pump to draw the aerosol into the chamber, with a sample substrate attached to the electrode wherein an electric field between the grounded chamber and electrode focuses particles on the substrate for analysis.

The invention also involves a method for detecting nanometer sized virus in a sample, by eliminating components from the mixture which interfere with the detection of the nanometer sized virus, the method comprising subjecting the sample suspected of containing said nanometer sized virus to an improved Integrated Virus Detection System which has been modified to incorporate an aerosol collecting means or an electrostatic collecting means into the improved Integrated Virus Detection System. The sample to be tested comprises air, water, soil, sand or plant or animal matter. The separation is within 4 mm resolution power. Also contemplated by the invention is a method for collecting and further analyzing nanometer sized particles selected from the group consisting of viruses, polystyrene latex (PSL) particles, and MS2 from a sample selected from the group consisting of air, water, soil, sand and plants and animals.

The herein disclosed invention shows that improvements can be made in the IVDS.

Separation of particles is possible with IVDS hardware and the improvements provided by this invention.

Collection of small particles (viruses and PSL particles) is possible through several techniques such as aerosol and electrostatic collection.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. An improved system for detecting and classifying submicron-sized particles in a sample taken from the environment, said system comprising an Integrated Virus Detection System (IVDS) of the type wherein the detecting means includes a differential mobility analyzer (DMA) and a condensation particle counter (CPC), wherein the improvement comprises an electrostatic collector positioned between the differential mobility analyzer and the condensation particle counter, wherein the electrostatic collector is fluidically connected to and receives the outlet air flow from the differential mobility analyzer and comprises a grounded sampling chamber having an airflow inlet and an outlet, an electrode disposed within the chamber, and a sample substrate attached to the electrode wherein an electric field between the grounded chamber and electrode focuses submicron-sized particles on the substrate for collection of submicron-sized particles from the airflow.

2. The system of claim 1, wherein the substrate comprises an electrically conductive material.

3. The system of claim 2, wherein the substrate comprises stainless steel foil.

4. The system of claim 1, wherein the electrode provides a negative potential of up to 10,000 volts.

5. The system of claim 1, further comprising a pump to draw aerosol airflow into the chamber.

6. The system of claim 1, wherein said outlet air flow is about 50 nanoliters per minute.

* * * * *